United States Patent
Guillonneau et al.

[11] Patent Number: 6,162,811
[45] Date of Patent: *Dec. 19, 2000

[54] ELLIPTICINE COMPOUNDS

[75] Inventors: Claude Guillonneau, Clamart; Yves Charton, Sceaux; Emile Bisagni, Orsay; Ghanem Atassi, Saint Cloud; Alain Pierre, Les Alluets le Roi; Nicolas Guilbaud, La Celle Saint Cloud, all of France

[73] Assignee: Adir et Compagnie, Courbevoie, France

[*] Notice: This patent issued on a continued prosecution application filed under 37 CFR 1.53(d), and is subject to the twenty year patent term provisions of 35 U.S.C. 154(a)(2).

[21] Appl. No.: 08/999,364

[22] Filed: Dec. 29, 1997

[30] Foreign Application Priority Data

Dec. 30, 1996 [FR] France .................................. 96 16165

[51] Int. Cl.$^7$ .................... A61K 31/4745; C07D 471/04
[52] U.S. Cl. ............................... 514/285; 546/70
[58] Field of Search ................ 546/70; 514/285

[56] References Cited

U.S. PATENT DOCUMENTS 3,933,827 1/1976 Brossi ........................................ 546/70
5,407,940 4/1995 Bisagni ..................................... 514/285
5,605,904 2/1997 Tsujihara .................................. 514/285

OTHER PUBLICATIONS

Tsujihara et al. in Chem. Pharm. Bull. 45(7) 1156–1162 (1997).

*Primary Examiner*—Evelyn Mei Huang
*Attorney, Agent, or Firm*—The firm of Gordon W. Hueschen

[57] ABSTRACT

The compounds of formula:

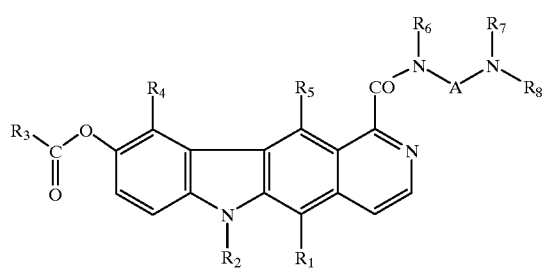

wherein $R_1$, $R_2$, $R_3$, $R_4$, $R_5$, $R_6$, $R_7$, $R_8$ and A are as defined in the description, their optical isomers and N-oxides, and pharmaceutically acceptable addition salts thereof with an acid or base, and the use thereof as anti-tumor agents.

9 Claims, No Drawings

ELLIPTICINE COMPOUNDS

The present invention relates to new olivacine or ellipticine compounds, to a process for their preparation and to pharmaceutical compositions containing them.

The compounds of the present invention are used in therapeutics by virtue of their anti-tumour activity.

A number of compounds of the olivacine or ellipticine family are already known for their anti-cancer properties, see Patent Application EP 0 591 058 A1.

The needs of therapy call for the constant development of new anti-cancer agents with the objective of obtaining compounds that are both more active and better tolerated.

The present invention relates to olivacine or ellipticine compounds that, relative to the nearest compounds of the prior art, are structurally novel (since the substitution at position 9 of the tetracycle differs from that of the known compounds) and toxicologically novel (the compounds of the present invention are better tolerated than the compounds described in the prior art) and demonstrate better in vivo activity relative to the reference products.

The present invention relates especially to:
compounds of formula I:

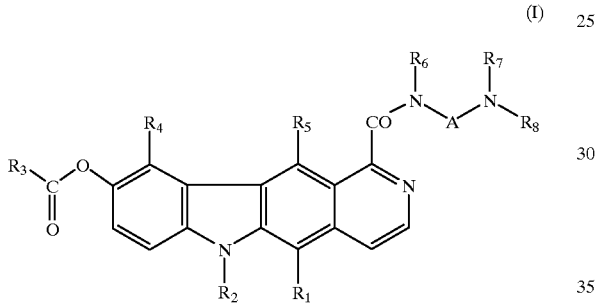

(I)

wherein:
$R_1$ represents an alkyl radical having from 1 to 6 carbon atoms in a straight or branched chain;

$R_2$, $R_5$ and $R_6$, which may be the same or different, each represents a hydrogen atom or an alkyl radical having from 1 to 6 carbon atoms in a straight or branched chain;

$R_3$ represents:
A) a hydrogen atom,
B) a $(C_3-C_8)$cycloalkyl group, or a $(C_1-C_{20})$alkyl, $(C_2-C_{20})$alkenyl or $(C_4-C_{20})$alkadienyl group, each of those being in a straight or branched chain, and each of the 4 groups being unsubstituted or substituted by from 1 to 3 groups selected from the radicals:
  a) $(C_1-C_6)$alkoxy;
  b) carboxy, $(C_1-C_6)$alkoxy-carbonyl and benzyloxycarbonyl;
  c) mono-, bi- or tri-cyclic aryl, or heteroaryl containing from 1 to 3 hetero atoms selected from the atoms nitrogen, oxygen and sulphur, each of which is partially or totally hydrogenated;
C) a mono-, bi- or tri-cyclic aryl group that is optionally totally or partially hydrogenated, or a heteroaryl group containing from 1 to 3 5-membered and/or 6-membered rings and having from 1 to 3 hetero atoms selected from the atoms nitrogen, oxygen and sulphur, such as, for example, a pyridyl, piperidyl, piperazinyl, pyrimidinyl, thienyl, benzothienyl, furyl, pyranyl, benzofuranyl, chromenyl, chromanyl, pyrrolyl, imidazolyl or quinolyl group; it being possible for each of the aryl and heteroaryl groups defined above optionally to be substituted by form 1 to 3 substituents selected from the radicals:
  a) $(C_1-C_6)$alkoxy-carbonyl,
  b) benzyloxycarbonyl,
  c) $(C_1-C_6)$alkyl each in a linear or branched chain, and each unsubstituted or substituted by one or two phenyl groups,
  d) $(C_1-C_6)$alkoxy each in a linear or branched chain, and
  e) carboxy;
D) an amino group that is mono- or di-substituted by one or two substituents selected from the radicals:
  a) $(C_1-C_6)$alkyls that are each unsubstituted or substituted by one or two substituents each selected from the radicals: carboxy, $(C_1-C_6)$alkoxy-carbonyl and benzyloxycarbonyl,
  b) aryl and heteroaryl, each being mono- or bi-cyclic, and each of those being partially or totally hydrogenated, and all being unsubstituted or substituted by one or two groups each selected from the radicals carboxy, $(C_1-C_6)$alkoxy-carbonyl and benzyloxycarbonyl; or
E) an amino group that is included in a 5-membered or 6-membered ring, optionally containing a second hetero atom selected from the atoms nitrogen, oxygen and sulphur, and that is optionally substituted by one or two groups each selected from the radicals $(C_1-C_6)$alkyl, benzhydryl, $(C_1-C_6)$alkoxy, $(C_1-C_6)$alkoxy-carbonyl, benzyloxycarbonyl, carboxy and piperidino;

$R_4$ represents:
a hydrogen atom,
a $(C_1-C_6)$alkyl radical in a straight or branched chain, optionally substituted by a di$(C_1-C_6)$alkylamino group, or
a $(C_2-C_6)$alkene radical;

$R_7$ and $R_8$, which may be the same or different, each represents a hydrogen atom, or a $(C_1-C_6)$alkyl or $(C_2-C_6)$alkenyl radical each in a straight or branched chain, or $R_7$ and $R_8$ may form, together with the nitrogen atom to which they are bonded, a heterocycle, optionally containing a second hetero atom selected from the atoms nitrogen, oxygen and sulphur, such as, for example, the pyrrole, pyrroline, pyrrolidine, imidazole, imidazoline, imidazolidine, oxazole, oxazoline, oxazolidine, pyridine, piperidine, morpholine, thiomorpholine, piperazine, pyrazole, pyrazoline, pyridazine, pyrimidine and pyrazine rings, and, in addition, $R_7$ may be bonded to $R_6$ in order together to form a —$(CH_2)_m$-bridge wherein m is 2 or 3; and A represents a linear or branched saturated hydrocarbon chain having form 1 to 10 carbon atoms, and also their possible optical isomers and N-oxides, and pharmaceutically acceptable addition salts thereof with an acid or base.

The invention relates also to a process for the preparation of compounds of formula I which is characterised in that:
a compound of formula II:

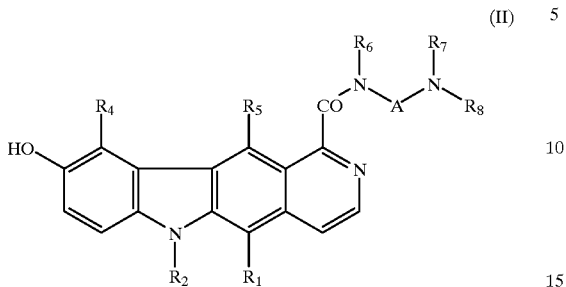

(II)

wherein:
$R_1$, $R_2$, $R_4$, $R_5$, $R_6$, $R_7$, $R_8$ and A are as defined above, is esterified using a compound selected from those that correspond to the formulae:

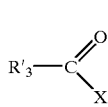

(IIIa)

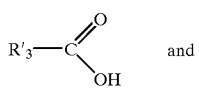 and (IIIb)

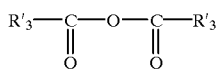

(IIIc)

wherein:
X represents a labile atom or group, such as, for example, a halogen atom, and
$R'_3$ represents:
  α) a $(C_3-C_8)$cycloalkyl group, or a $(C_1-C_{20})$alkyl, $(C_2-C_{20})$alkenyl or $(C_4-C_{20})$alkadienyl group, each of those being in a straight or branched chain, and each of the 4 groups being unsubstituted or substituted by from 1 to 3 groups selected from the radicals:
    a) $(C_1-C_6)$alkoxy;
    b) $(C_1-C_6)$alkoxy-carbonyl and benzyloxycarbonyl; and
    c) mono-, bi- or tri-cyclic aryl, or heteroaryl containing from 1 to 3 hetero atoms selected from the atoms nitrogen, oxygen and sulphur;
  β) mono-, bi- or tri-cyclic aryl group that is optionally totally or partially hydrogenated, or a heteroaryl group containing from 1 to 3 5-membered and/or 6-membered rings and having from 1 to 3 hetero atoms selected from the atoms nitrogen, oxygen and sulphur, such as, for example, a pyridyl, piperidyl, piperazinyl, pyrimidinyl, thienyl, benzothienyl, furyl, pyranyl, benzofuranyl, chromenyl, chromanyl, pyrrolyl, imidazolyl or quinolyl group;
  it being possible for each of the aryl and heteroaryl groups defined above optionally to be substituted by from 1 to 3 substituents selected from the radicals:
    a) $(C_1-C_6)$alkoxy-carbonyl,
    b) benzyloxycarbonyl,
    c) $(C_1-C_6)$alkyl each in a linear or branched chain, and each unsubstituted or substituted by one or two phenyl groups, and
    d) $(C_1-C_6)$alkoxy each in a linear or branched chain;
  γ) an amino group that is di-substituted by two substituents each selected from the radicals:
    a) $(C_1-C_6)$alkyls that are each unsubstituted or substituted by one or two substituents each selected from the radicals: $(C_1-C_6)$alkoxy-carbonyl and benzyloxycarbonyl, and
    b) aryl and heteroaryl, each being mono- or bi-cyclic, and each of those being partially or totally hydrogenated, and all being unsubstituted or substituted by one or two groups each selected from the radicals $(C_1-C_6)$-alkoxy-carbonyl and benzyloxycarbonyl; and
  δ) an amino group that is included in a 5-membered or 6-membered ring, optionally containing a second hetero atom selected from the atoms nitrogen, oxygen and sulphur, and that is optionally substituted by one or two groups each selected from the radicals $(C_1-C_6)$alkyl, benzhydryl, $(C_1-C_6)$alkoxy, $(C_1-C_6)$alkoxy-carbonyl, benzyloxycarbonyl and piperidino;
to obtain compounds of formula Ia:

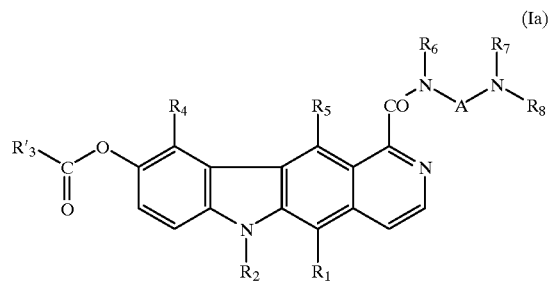

(Ia)

wherein $R_1$, $R_2$, $R'_3$, $R_4$, $R_5$, $R_6$, $R_7$, $R_8$ and A are as defined above:
compounds of formula Ia wherein $R'_3$ includes as substituent at least one benzyloxy group, that is to say compounds that correspond more specifically to the formula I'a:

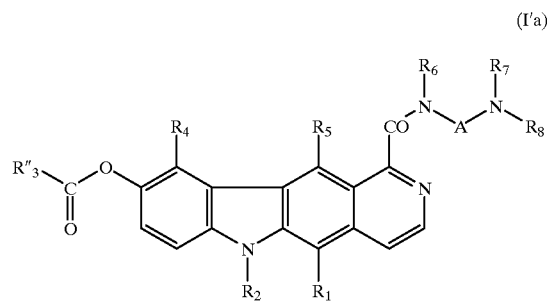

(I'a)

wherein:
$R_1$, $R_2$, $R_4$, $R_5$, $R_6$, $R_7$, $R_8$ and A are as defined above and
$R''_3$ represents:
  α) a $(C_3-C_8)$cycloalkyl group, or a $(C_1-C_{20})$alkyl group in a straight or branched chain, each of those groups being substituted by from 1 to 3 benzyloxycarbonyl radicals;

β) a mono-, bi- or tri-cyclic aryl group that is optionally totally or partially hydrogenated, or a heteroaryl group containing from 1 to 3 5-membered and/or 6-membered rings and having from 1 to 3 hetero atoms selected from the atoms nitrogen, oxygen and sulphur, such as, for example, a pyridyl, piperidyl, piperazinyl, pyrimidinyl, thienyl, benzothienyl, furyl, pyranyl, benzofuranyl, chromenyl, chromanyl, pyrrolyl, imidazolyl or quinolyl group;

each of the aryl and heteroaryl groups defined above being substituted by from 1 to 3 benzyloxycarbonyl radicals;

γ) an amino group that is mono- or di-substituted by one or two substituents selected from the radicals:
  a) $(C_1-C_6)$alkyls that are each substituted by one or two benzyloxycarbonyl radicals,
  b) aryl and heteroaryl, each being mono- or bi-cyclic, and each of those being partially or totally hydrogenated, and all being substituted by one or two benzyloxycarbonyl radicals;

δ) an amino group that is included in a 5-membered or 6-membered ring, optionally containing a second hetero atom selected from the atoms nitrogen, oxygen and sulphur, and that is substituted by one or two benzyloxycarbonyl radicals, are treated with hydrogen or with a hydrogen donor (such as, for example, cyclohexene) to obtain the corresponding compounds wherein any benzyloxycarbonyl substituent in the starting compound of formula I'a has been replaced by a carboxy radical, that is to say to obtain compounds of formula Ib:

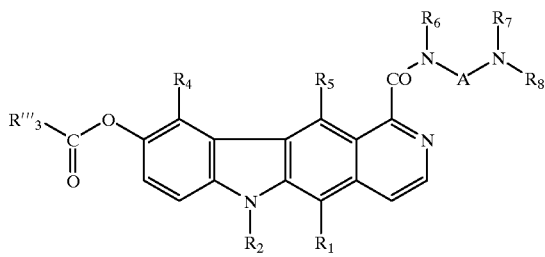

(Ib)

wherein:
  $R_1$, $R_2$, $R_4$, $R_5$, $R_6$, $R_7$, $R_8$ and A are as defined above and
  $R'''_3$ represents:
    α) a $(C_3-C_8)$cycloalkyl group, or a $(C_1-C_{20})$alkyl group in a straight or branched chain, each of those groups being substituted by from 1 to 3 carboxy radicals,
    β) a mono-, bi- or tri-cyclic aryl group that is optionally totally or partially hydrogenated, or a heteroaryl group containing from 1 to 3 5-membered and/or 6-membered rings and having from 1 to 3 hetero atoms selected from the atoms nitrogen, oxygen and sulphur, such as, for example, a pyridyl, piperidyl, piperazinyl, pyrimidinyl, thienyl, benzothienyl, furyl, pyranyl, benzofuranyl, chromenyl, chromanyl, pyrrolyl, imidazolyl or quinolyl group;
    each of the aryl and heteroaryl groups defined above being substituted by from 1 to 3 carboxy radicals;
    γ) an amino group that is mono- or di-substituted by one or two substituents selected from the radicals:
      a) $(C_1-C_6)$alkyls that are each substituted by one or two carboxy radicals,
      b) aryl and heteroaryl, each being mono- or bi-cyclic, and each of those being partially or totally hydrogenated, and all being substituted by one or two carboxy radicals;
    δ) an amino group that is included in a 5-membered or 6-membered ring, optionally containing a second hetero atom selected from the atoms nitrogen, oxygen and sulphur, and that is substituted by one or two carboxy radicals;

and a compound of formula II as defined above is reacted with a mixture of formic acid and acetic anhydride to obtain compounds of formula I wherein $R_3$ represents a hydrogen atom, that is to say to obtain compounds of formula Ic:

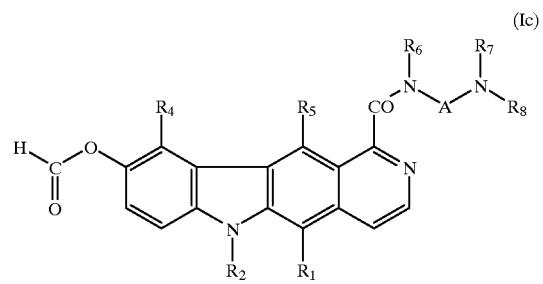

(Ic)

wherein $R_1$, $R_2$, $R_4$, $R_5$, $R_6$, $R_7$, $R_8$ and A are as defined above.

The totality of the compounds of formulae Ia, Ib and Ic form the totality of the compounds of formula I.

The present invention relates also to a process for the preparation of:

compounds of formula I wherein the meaning of $R_3$ is limited to a $(C_1-C_{20})$alkyl radical that is substituted by a carboxy radical, that is to say:

compounds that correspond more specifically to formula I' (itself included in formula Ib):

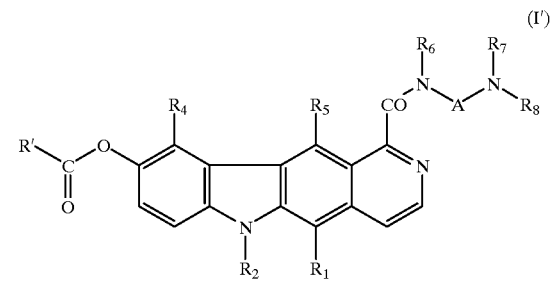

(I')

wherein:
  $R_1$, $R_2$, $R_4$, $R_5$, $R_6$, $R_7$, $R_8$ and A are as defined above, and
  R' represents a $(C_1-C_{20})$alkyl radical that is substituted by a carboxy radical, characterised in that compounds of formula I":

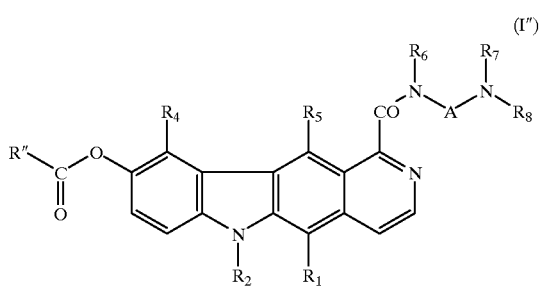

(I")

wherein:

$R_1$, $R_2$, $R_4$, $R_5$, $R_6$, $R_7$, $R_8$ and A are as defined above, and

R" represents a $(C_1-C_{20})$alkyl radical that is substituted at the end of the chain by a benzyloxy radical, are treated with hydrogen or with a hydrogen donor (such as, for example, cyclohexene).

A number of compounds of formula I' can be obtained by reacting a compound of formula II with a cyclic anhydride of formula:

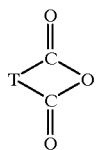

wherein T represents a saturated hydrocarbon chain having from 2 to 10 carbon atoms that is optionally substituted by one or two $(C_1-C_5)$alkyl radicals.

That process also forms part of the present invention.

The present invention relates also to a process for the preparation of:

compounds of formula I wherein the meaning of $R_3$ is limited to an amino group that is monosubstituted by either:
  a $(C_1-C_6)$alkyl radical that is unsubstituted or substituted by one or two substituents selected from the radicals $(C_1-C_6)$alkoxy-carbonyl and benzyloxycarbonyl, or
  a mono- or bi-cyclic aryl or heteroaryl radical that is optionally totally or partially hydrogenated and that is unsubstituted or substituted by one or two groups each selected from the radicals $(C_1-C_6)$alkoxy-carbonyl and benzyloxycarbonyl, that is to say compounds that correspond more specifically to the formula I'" (itself included in formula Ia):

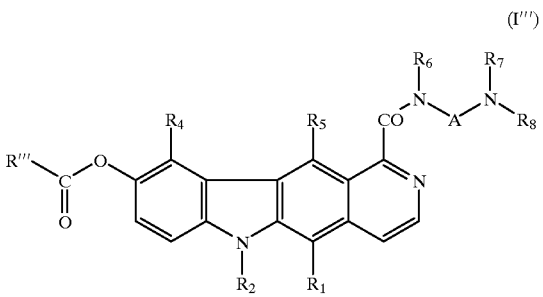

(I'")

wherein:

$R_1$, $R_2$, $R_4$, $R_5$, $R_6$, $R_7$, $R_8$ and A are as defined above, and

R'" represents an amino group that is monosubstituted by either:
  a $(C_1-C_6)$alkyl radical that is unsubstituted or substituted by one or two substituents selected from the radicals $(C_1-C_6)$alkoxy-carbonyl and benzyloxycarbonyl, or
  a mono- or bi-cyclic aryl or heteroaryl radical that is optionally totally or partially hydrogenated and that is unsubstituted or substituted by one or two groups each selected from the radicals $(C_1-C_6)$ alkoxy-carbonyl and benzyloxycarbonyl, characterised in that:

a compound of formula II defined above is reacted with an isocyanate of formula IV:

$$R_9\text{—N=C=O} \qquad \text{(IV)}$$

wherein:

$R_9$ represents either:
  a $(C_1-C_6)$alkyl radical that is unsubstituted or substituted by one or two substituents selected from the radicals $(C_1-C_6)$alkoxy-carbonyl and benzyloxycarbonyl, or
  a mono- or bi-cyclic aryl or heteroaryl radical that is optionally totally or partially hydrogenated and that is unsubstituted or substituted by one or two groups each selected from the radicals $(C_1-C_6)$ alkoxy-carbonyl and benzyloxycarbonyl.

It is especially advantageous to react the compounds of formulae IIIa, IIIc and IV with a compound of formula II, optionally in the presence of an acceptor for the hydracid formed in the course of the reaction, in a solvent, such as, for example, tetrahydrofuran, dioxane, dichloromethane, dichlorobenzene, dimethylformamide or pyridine, at a temperature of from 20 to 80° C. As acceptor there may be used, for example, an alkali metal carbonate, such as potassium carbonate, a tertiary amine, such as triethylamine, dimethylaminopyridine (DMAP) or 1,8-diazabicyclo[5.4.0]undec-7-ene (DBU).

The reaction of the compounds of formula II with the compounds of formula IIIb is appropriately carried out, in the presence of a coupling agent, such as dicyclohexylcarbodiimide optionally in the presence of 1-hydroxybenzotriazole, 1-ethyl-3-(3-dimethylaminopropyl)carbodiimide or 1,1-carbonyldiimidazole, in an aprotic solvent, such as tetrahydrofuran or dimethylformamide.

The reaction of the compounds of formula I'a with hydrogen or with a hydrogen donor, such as cyclohexene, is advantageously carried out in a solvent, such as water, ethanol or dimethylformamide, in the presence of a hydrogenation catalyst, such as palladium-on-carbon or palladium hydroxide, under a pressure of from 1×10⁵ Pa to 5×10⁵ Pa, at a temperature of from 20 to 80° C.

Compounds of formula H used as starting materials are either described in patent specification EP 0 591 058 A$_1$, or are prepared from known products described in patent specification EP 0 591 058 A$_1$ for the preparation of analogous products.

The other compounds used as starting materials are either commercial products or products that are prepared from known substances in accordance with conventional methods of organic synthesis already described in the literature.

The compounds of formula I yield salts with physiologically tolerable acids or bases, which salts are, as such, also included in the present invention.

The compounds of formula I also yield N-oxide compounds which, as such, are also included in the present invention.

A number of compounds of formula I include one or more asymmetric carbon atoms and thus yield enantiomers or diastereoisomers, which also form part of the present invention.

The compounds of the present invention have very valuable pharmacological properties, especially an excellent in vitro cytotoxicity and an in vivo anti-tumour activity that is superior to that of the compounds of the prior art, which, added to the fact that they are especially well tolerated, enables them to be used therapeutically as anti-tumour agents.

Especially valuable and especially representative of the invention are compounds of formula I wherein:

R$_1$ and R$_2$ each represents a methyl radical;

R$_3$ represents a carboxyalkyl radical wherein the alkyl moiety contains from 1 to 8 carbon atoms in a straight or branched chain;

R$_4$ and R$_5$, which may be the same or different, each represents a hydrogen atom or a methyl radical;

R$_6$ represents a hydrogen atom;

R$_7$ and R$_8$ each represents a methyl radical, and

A represents —(CH$_2$)$_2$— or (CH$_2$)$_3$;

their possible optical isomers and N-oxides, and pharmaceutically acceptable addition salts thereof with an acid or base.

The present invention relates also to pharmaceutical compositions comprising as active ingredient at least one compound of the present invention, mixed with or in association with one or more pharmaceutical excipients or inert non-toxic carriers.

The pharmaceutical compositions are generally in unit dose form suitable for oral, rectal or parenteral administration, especially tablets, dragées, gelatin capsules, suppositories and injectable or drinkable solutions.

The dosage varies according to the age and weight of the patient, the mode of administration, the nature of the therapeutic indication and any associated treatments, and ranges from 0.1 to 400 mg daily, administered in one or more doses.

The following Examples illustrate the present invention, the melting points being determined using a Kofler plate (K) or a capillary tube (cap.) The silica used for purification is Amicon silica (0.035–0.07 mm). The pressure used is 10⁵ Pa.

EXAMPLE 1

1-[(2-Dimethylaminoethyl)aminocarbonyl]-5,6-dimethyl-9-tetradecanoyloxy-6H-pyrido-[4,3-b]carbazole

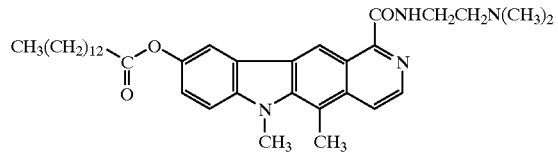

2 g of 1-[(2-dimethylaminoethyl)aminocarbonyl]-5,6-dimethyl-9-hydroxy-6H-pyrido[4,3-b]-carbazole are dissolved in 60 ml of pyridine. The mixture is cooled to 5° C. and then 4.67 g of myristic anhydride are introduced over a period of 3 minutes. The mixture is stirred at 5° C. for 2 hours and then at room temperature for 16 hours, and concentrated to dryness at a temperature of less than 40° C. The residue is chromatographed on 150 g of silica using a mixture of dichloromethane and methanol as eluant. 2.4 g of the desired product are obtained, m.p.(K): 98° C.

EXAMPLES 2 to 10

By proceeding as described in Example 1, the compounds of the following Examples were prepared:

2) 1-[(2-Dimethylaminoethyl)aminocarbonyl]-5,6-dimethyl-9-acetoxy-6H-pyrido-[4,3-b]carbazole, m.p.(K): 166° C.

3) 1-[(2-Dimethylaminoethyl)aminocarbonyl]-5,6-dimethyl-9-(4-carboxybutanoyloxy)-6H-pyrido-[4,3-b]carbazole dihydrochloride, m.p.(cap): 190–200° C.

4) 1-[(2-Dimethylaminoethyl)aminocarbonyl]-5,6-dimethyl-9-(5-carboxypentanoyloxy)-11-methyl-6H-pyrido[4,3-b]carbazole dihydrochloride, m.p.(cap): 180° C. (decomposition).

5) 1-[(2-Dimethylaminoethyl)aminocarbonyl]-5,6-dimethyl-9-(6-carboxyhexanoyloxy)-6H-pyrido[4,3-b]carbazole dihydrochloride, m.p.: 190–196° C.

6) 1-[(2-Dimethylaminoethyl)aminocarbonyl]-5,6-dimethyl-9-(7-carboxyheptanoyloxy)-6H-pyrido[4,3-b]carbazole dihydrochloride, m.p.(cap): 210–215° C.

7) 1-[(2-Dimethylaminoethyl)aminocarbonyl]-5,6,-dimethyl-9-(4-carboxy-3,3-dimethyl-butanoyloxy)-6H-pyrido[4,3-b]carbazole dihydrochloride, m.p.(cap): 190° C. (decomposition).

8) 1-[(2-Dimethylaminoethyl)aminocarbonyl]-5,6,10-trimethyl-9-(5-carboxypentanoyloxy)-6H-pyrido[4,3-b]carbazole dihydrochloride, m.p.(cap): 215–225° C.

9) 1-[(2-Dimethylaminoethyl)aminocarbonyl]-5,6,11-trimethyl-9-(5-carboxypentanoyloxy)-6H-pyrido[4,3-b]carbazole dihydrochloride, m.p.(cap): 185–195° C.

10) 1-[(2-Dimethylaminoethyl)aminocarbonyl]-5,6-dimethyl-9-(4-carboxy-3-methyl-butanoyloxy)-6H-pyrido-[4,3-b]carbazole, m.p. (cap): 170–175° C.

EXAMPLE 11

(R,S)-1-[(2-Dimethylaminoethyl)aminocarbonyl]-5,
6-dimethyl-9-(trans-phenylcyclopropyl-carboxy)-
6H-pyrido[4,3-b]carbazole

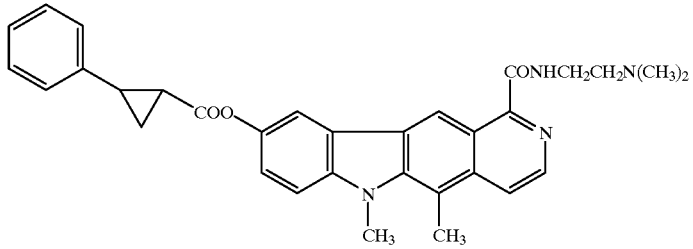

1 g of 1-[(2-Dimethylaminoethyl)aminocarbonyl]-5,6-dimethyl-9-hydroxy-6H-pyrido[4,3-b]-carbazole and 0.29 g of triethylamine are dissolved in 50 ml of tetrahydrofuran. The mixture is cooled to 5° C. and, over a period of 15 minutes, 0.53 g of (R,S)-trans-2-phenylcyclopropylcarboxylic acid chloride dissolved in 5 ml of tetrahydrofuran is introduced. The mixture is stirred at 5° C. for 1 hour and then at room temperature for 20 hours, and concentrated to dryness. The residue is taken up in dichloromethane, washed with water, dried over sodium sulphate and concentrated to dryness. Chromatography is carried out on 70 g of silica using a mixture of dichloromethane and methanol (90:10) as eluant. 0.9 g of the desired product is obtained, m.p.(cap): 176–178° C.

EXAMPLES 12 to 15

By proceeding as described in Example 11, the compounds of the following Examples were prepared:

12) 1-[(2-Dimethylaminoethyl)aminocarbonyl]-5,6-dimethyl-9-(4-methoxycarbonylbutanoyl-oxy)-6H-pyrido[4,3-b]carbazole, m.p.(cap): 120–122° C.
13) 1-[(2-Dimethylaminoethyl)aminocarbonyl]-5,6-dimethyl-9-(2-phenylacetoxy)-6H-pyrido[4,3-b]carbazole, m.p.(cap): 84–86° C.
14) 1-[(2-Dimethylaminoethyl)aminocarbonyl]-5,6-dimethyl-9-nonanoyloxy-6H-pyrido-[4,3-b]carbazole, m.p.(cap): 122–125° C.
15) 1-[(2-Dimethylaminoethyl)aminocarbonyl]-5,6-dimethyl-9-[3-ethoxypropanoyloxy]-6H-pyrido[4,3-b]carbazole, m.p.(cap): 116–118° C.

EXAMPLE 16

1-[(2-Dimethylaminoethyl)aminocarbonyl]-5,6-
dimethyl-9-[3-benzyloxycarbonylpropanoyl-oxy]-
6H-pyrido[4,3-b]carbazole 4.5 g succinic acid benzyl monoester, 4.95 g of dicyclohexylcarbodiimide, 2.85 g of 1-hydroxybenzotriazole and 240 ml of dimethylformamide are stirred for 4 hours at room temperature. 3 g of 1-[(2-dimethylaminoethyl)aminocarbonyl]-5,6-dimethyl-9-hydroxy-6H-pyrido[4,3-b]carbazole are added and the mixture is stirred at room temperature for 16 hours and concentrated to dryness. The residue is taken up in dichloromethane, washed with a saturated sodium hydrogen carbonate solution, dried over sodium sulphate and concentrated to dryness. The residue is chromatographed on 280 g of silica using a mixture of toluene, ethanol and triethylamine (90:10:0.5) as eluant. The desired fractions are concentrated to dryness and the residue is taken up in ethanol and concentrated to dryness again. The residue is taken up in ether, suction-filtered and dried at 60° C. under 13.328 Pa. 3.3 g of the desired product are obtained, m.p.(cap): 174–176° C.

EXAMPLES 17 and 18

By proceeding as described in Example 16, the compounds of the following Examples were prepared:

17) 1-[(2-Dimethylaminoethyl)aminocarbonyl]-5,6-dimethyl-9-(5-benzyloxycarbonyl-pentanoyloxy)-6H-pyrido[4,3-b]carbazole, m.p.(cap): 88–90° C.
18) (R,S)-{[1-(2-Dimethylaminoethyl)aminocarbonyl]-5,6-dimethyl-6H-pyrido[4,3-b]carbazol-9-yl} ester of 5-[di[1,2]thiolan-3-yl]pentanoic acid, m.p.(cap): 140–142° C.

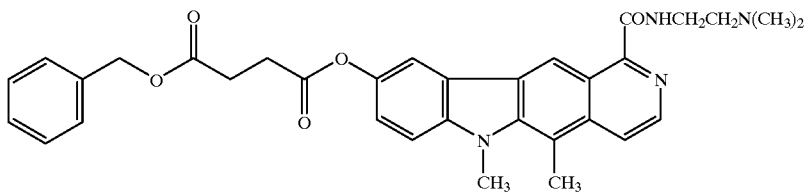

EXAMPLE 19

1-[(2-Dimethylaminoethyl)aminocarbonyl]-5,6-dimethyl-9-acetoxy-6H-pyrido[4,3-b]carbazole N-oxide dihydrochloride

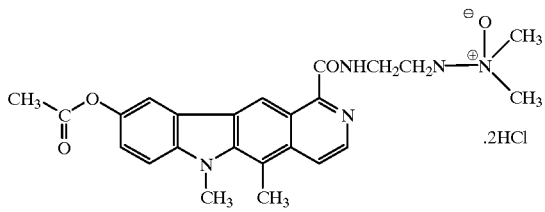

The reaction of 1-[(2-dimethylaminoethyl)aminocarbonyl]-5,6-dimethyl-9-acetoxy-6H-pyrido-[4,3-b]carbazole with 3-chloroperoxybenzoic acid in dichloromethane at room temperature results in the desired product, m.p.(cap): 120° C. (decomposition).

EXAMPLE 20

1-[(2-Dimethylaminoethyl)aminocarbonyl]-5,6-dimethyl-9-(4-piperidinopiperidinocarbonyloxy)-6H-pyrido[4,3-b]carbazole

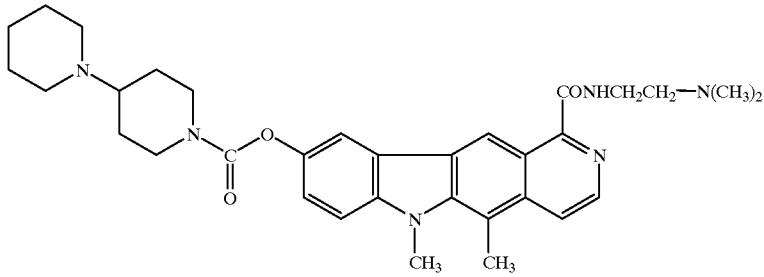

1.6 g of 1-[(2-dimethylaminoethyl)aminocarbonyl]-5,6-dimethyl-9-hydroxy-6H-pyrido[4,3-b]carbazole and 1.5 g of 4-piperidinopiperidine N-chloroformate are stirred in 80 ml of pyridine for 16 hours. The mixture is concentrated to dryness, and the residue is taken up in dichloromethane, washed with a 10% sodium hydrogen carbonate solution, dried over sodium sulphate and concentrated to dryness. Dioxane is added and the mixture is concentrated to dryness again to remove the residual pyridine. Trituration is carried out in a mixture of ethyl acetate and ether. Suction-filtration is carried out, followed by washing with ether and drying at 50° C. under 66 Pa. 2.3 g of the desired product are obtained, m.p.(cap): 190–200° C.

EXAMPLES 21 to 27

By proceeding as described in Example 20, the compounds of the following Examples were prepared:

21) 1-[(2-Dimethylaminoethyl)aminocarbonyl]-5,6-dimethyl-9-(N-methyldodecylaminocarbonyloxy)-6H-pyrido[4,3-b]carbazole, m.p.(cap): 90–93° C.
22) 1-[(2-Dimethylaminoethyl)aminocarbonyl]-5,6-dimethyl-9-(N-phenyl-N-methylaminocarbonyloxy)-6H-pyrido[4,3-b]carbazole, m.p.(cap): 125–128° C.
23) 1-[(2-Dimethylaminoethyl)aminocarbonyl]-5,6-dimethyl-9-dimethylaminocarbonyloxy-6H-pyrido[4,3-b]carbazole, m.p.(cap): 188–190° C.
24) 1-[(2-Dimethylaminoethyl)aminocarbonyl]-5,6-dimethyl-9-morpholinocarbonyloxy-6H-pyrido[4,3-b]carbazole, m.p.(cap): 190–192° C.
25) 1-[(2-Dimethylaminoethyl)aminocarbonyl]-5,6-dimethyl-9-[(4-benzhydrylpiperazin-1-yl)carbonyloxy]-6H-pyrido[4,3-b]carbazole, m.p.(cap): 135–138° C.
26) 1-[(2-Dimethylaminoethyl)aminocarbonyl]-5,6-dimethyl-9-(4-methylpiperazino-carbonyloxy)-6H-pyrido[4,3-b]carbazole, m.p.(cap): 134–137° C.
27) 1-[(2-Dimethylaminoethyl)aminocarbonyl]-5,6-dimethyl-9-(4-benzyloxycarbonyl-piperazinocarbonyloxy)-6H-pyrido[4,3-b]carbazole, m.p.(cap): 186–188° C.

EXAMPLE 28

1-[(2-Dimethylaminoethyl)aminocarbonyl]-5,6-dimethyl-9-(docecylaminocarbonyloxy)-6H-pyrido[4,3-b]carbazole

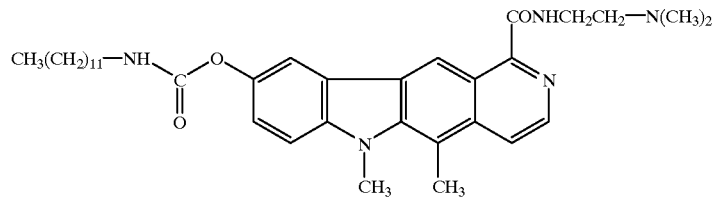

3.8 g of 1-[(2-dimethylaminoethyl)aminocarbonyl]-5,6-dimethyl-9-hydroxy-6H-pyrido-[4,3-b]carbazole, 3.2 g of n-dodecyl isocyanate and 0.05 g of 1,8-diazabicyclo[5.4.0]undec-7-ene are stirred in 50 ml of pyridine at 50° C. for 16 hours. The mixture is concentrated to dryness, dioxane is added, and concentration to dryness is carried out again. Chromatography is carried out on 480 g of silica using dichloromethane, methanol and ammonia (95:5:0.5) as eluant. The product obtained is stirred in ether, suction-filtered and dried at 50° C. under 66 Pa. 3.9 g of the desired product are obtained, m.p.(cap): 162–164° C.

EXAMPLES 29 to 31

By proceeding as described in Example 28, the compounds of the following Examples were prepared:

29) 1-[(2-Dimethylaminoethyl)aminocarbonyl]-5,6-dimethyl-9-[(2-ethoxycarbonylethyl)-aminocarbonyloxy]-6H-pyrido[4,3-b]carbazole, m.p. (cap): 120° C. (decomposition).
30) 1-[(2-Dimethylaminoethyl)aminocarbonyl]-5,6-dimethyl-9-[(3-benzyloxycarbonylpropyl) aminocarbonyloxy]-6H-pyrido[4,3-b]carbazole, m.p. (cap): 125–128° C.
31) 1-[(2-Dimethylaminoethyl)aminocarbonyl]-5,6-dimethyl-9-[(2-benzyloxycarbonylethyl) aminocarbonyloxy]-6H-pyrido[4,3-b]carbazole, m.p. (cap): 112–114° C.

EXAMPLE 32

1-[(2-Dimethylaminoethyl)aminocarbonyl]-5,6-dimethyl-9-(5-carboxypentanoyloxy)-6H-pyrido[4,3-b]carbazole

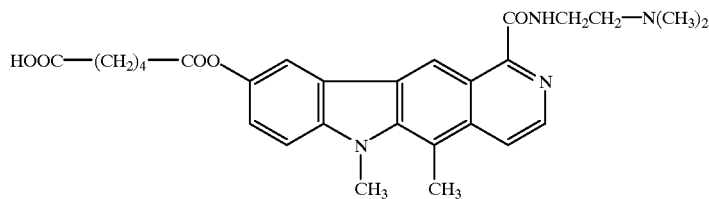

EXAMPLES 33–36

By proceeding as described in Example 32, the compounds of the following Examples were prepared:

33) 1-[(2-Dimethylaminoethyl)aminocarbonyl]-5,6-dimethyl-9-[(2-carboxyethylamino)-carbonyloxy]-6H-pyrido[4,3-b]carbazole, m.p.(cap) 195–198° C.
34) 1-[(2-Dimethylaminoethyl)aminocarbonyl]-5,6-dimethyl-9-[(3-carboxypropylamino)-carbonyloxy]-6H-pyrido[4,3-b]carbazole, m.p.(cap): 174–177° C.
35) 1-[(2-Dimethylaminoethyl)aminocarbonyl]-5,6-dimethyl-9-(5-carboxy-2,2,5,5-tetramethyl-pentanoyloxy)-6H-pyrido[4,3-b]carbazole, m.p. (cap): 191–193° C.
36) 1-[(3-Dimethylaminopropyl)aminocarbonyl]-5,6-dimethyl-9-[(4-carboxybutanoyloxy)-6H-pyrido[4,3-b]carbazole, m.p. (cap): 222–228° C.

EXAMPLE 37

1-[(2-Dimethylaminoethyl)aminocarbonyl]-5,6-dimethyl-9-(piperazinocarbonyloxy)-6H-pyrido[4,3-b]carbazole

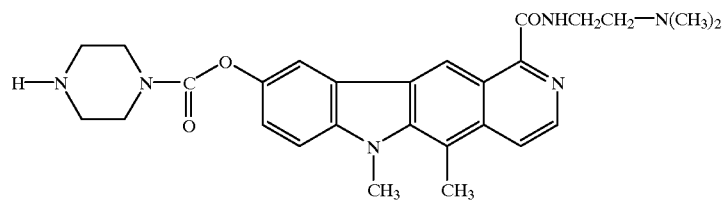

2 g of 1-[(2-dimethylaminoethyl)aminocarbonyl]-5,6-dimethyl-9-(5-benzyloxycarbonylpentan-oyloxy)-6H-pyrido[4,3-b]carbazole dissolved in 600 ml of methanol are hydrogenated in the presence of 0.2 g of palladium-on-barium sulphate for 36 hours under $3.5 \times 10^5$ Pa of hydrogen at room temperature. The catalyst is removed by filtration and the filtrate is concentrated to dryness. The residue is taken up in ethanol and concentrated almost to dryness, and diethyl ether is added. The precipitate is suction-filtered and dried at 40° C. under 133 Pa. 1.9 g of the desired product are obtained, m.p.(cap): 88–90° C.

2.6 g of 1-[(2-dimethylaminoethyl)aminocarbonyl]-5,6-dimethyl-9-[(4-benzyloxycarbonyl-piperazino) carbonyloxy]-6H-pyrido[4,3-b]carbazole, 5 ml of cyclohexene and 1 g of 10% palladium-on-carbon in 260 ml of methanol are refluxed for 45 minutes. The catalyst is removed by filtration and the filtrate is concentrated to dryness. The residue is chromatographed on silica using a mixture of dichloromethane, methanol and ammonia (85:15:1) as eluant. The product obtained is washed with diethyl ether and ethanol to yield 1.6 g of the desired product, m.p.(cap): 230–234° C.

EXAMPLE 38

1-[(2-Dimethylaminoethyl)aminocarbonyl]-5,6-dimethyl-9-(pyrid-3-ylcarbonyloxy)-6H-pyrido[4,3-b]carbazole.

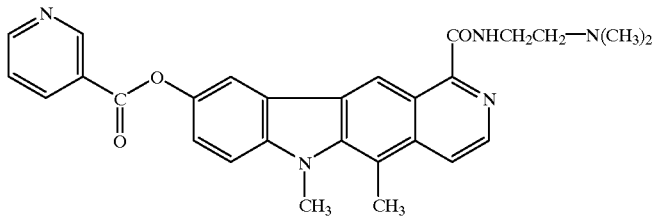

A mixture containing 3 g of 1-[(2-dimethylaminoethyl)aminocarbonyl]-5,6-dimethyl-9-hydroxy-6H-pyrido[4,3-b]carbazole, 1.5 g of nicotinic acid, 3.7 g of dicyclohexylcarbodiimide and 1.5 g of dimethylaminopyridine dissolved in 100 ml of pyridine is stirred at room temperature for 16 hours. At the end of 16 hours, a further 2 g of dicyclohexylcarbodiimide and 0.75 g of nicotinic acid are added and the mixture is stirred for a further 24 hours and concentrated to dryness. The residue is taken up in dichloromethane and washed with sodium hydrogen carbonate, and the dichloromethane phase is concentrated to remove by filtration as much as possible of the dicyclohexylurea formed, and the filtrate is concentrated to dryness. The residue is chromatographed on silica using a mixture of toluene, ethanol and triethylamine (100:10:05) as eluant. 3.5 g of the desired product are obtained, m.p. (cap): 190–192° C.

EXAMPLE 39

Pharmacological Study

A/In Vitro Activity: Cytotoxicity

Four cell lines were used:

1 murine leukaemia P388, 1 murine lung carcinoma, Lewis Lung Carcinoma (LLC), 1 human epidermoid carcinoma, KB-3-1, the corresponding resistant line, KB-A1, the multi-drug resistance of which was induced by adriamycin (ADR).

The cells are cultured in complete RPMI 1640 culture medium containing 10% foetal calf serum, 2 mM of glutamine, 50 units/ml of penicillin, 50 µg/ml of streptomycin and 10 mM of Hepes, pH=7.4.

The cells are distributed onto microplates and exposed to the cytotoxic compounds. The cells are then incubated for 2 days (P388) or 4 days (LLC, KB-A1, KB-3-1). The number of viable cells is then quantified by a colorimetric assay, the Microculture Tetrazolium Assay (Carmichael J., DeGraff W. G., Gazdar A. F., Minna J. D. and Mitchell J. R., Evaluation of a tetrazolium-based semiautomated colorimetric assay: assessment of chemosensitivity testing, Cancer Res., 47, 936–942, 1987).

The results are expressed in $IC_{50}$, which is the cytotoxicity concentration that inhibits the proliferation of the treated cells by 50%. The results obtained for the lines used are given in Table 1.

By way of example, there are listed below the results obtained with the compounds of Examples 2, 3 and 32, which are especially representative of the invention, and with adriamycin (ADR) as reference product.

TABLE 1

| Test compounds | IC50 (nM) | | | |
| --- | --- | --- | --- | --- |
| | P388 | LLC | KB-3-1 | KB-A1 |
| Example 2 | 5.8 | 13.5 | 36.1 | 758 |
| Example 3 | 7.1 | 43.2 | 74.2 | 923 |
| Example 32 | 5.1 | 3.5 | 40.6 | 757.9 |
| ADR | 18.1 | 19.3 | 17.3 | 6693 |

The cytotoxicity of the 3 test compounds is of the same order of magnitude as that of adriamycin on the sensitive lines. On the line KB-A1, which is adriamycin-resistant, the 3 test compounds are from 7 to 9 times more active than adriamycin. Those compounds may thus be used successfully against tumours that are adriamycin-resistant and that exhibit the multi-drug resistance phenotype.

B/In Vivo Activity

1/Anti-tumour Activity of the Compounds on Leukaemia P388

The line P388 (murine leukaemia) was supplied by the National Cancer Institute (Frederick, USA). The tumour cells ($10^6$ cells) were injected on day 0 into the peritoneal cavity of female BDF1 mice (Iffa-Credo, France) weighing from 18 to 20 g (groups of 6 or 7 animals).

The products were administered intravenously, at the doses indicated, on day 1 or on days 1, 5 and 9.

The anti-tumour activity is expressed in % T/C:

$$\% \, T/C = \frac{\text{median survival time of the treated animals}}{\text{median survival time of the control animals}} \times 100$$

The number of animals surviving 60 days (long-term survival) is indicated.

By way of example, Table 2 gives the results obtained with the compound of Example 32 which is especially representative of the invention.

TABLE 2

Anti-tumour activity of the compound of Example 32 administered i.v. to leukaemia P388 i.p.

| Administration on D1 of the compound of Example 32 (mg/kg) | T/C % (surviving to D60) |
|---|---|
| 0 | 100 |
| 20 | 125 |
| 40 | 154 |
| 80 | 186 |
| 160 | 233 |
| 240 | >600 (4/7) |
| 320 | >600 (6/7) |

| Administration on D1, 5 and 9 of the compound of Example 32 (mg/kg) | T/C % (surviving to D60) |
|---|---|
| 0 | 100 |
| 10 | 137 |
| 20 | 171 |
| 40 | 236 |
| 80 | >600 (6/7) |
| 160 | >600 (6/7) |

A study of this Table shows that:

administered i.v. on D1, the compound of Example 32 is active at from 20 to 320 mg/kg and cures 4 mice out of 7 at 240 mg/kg and 6 mice out of 7 at 320 mg/kg.

administered i.v. on days 1, 5 and 9, the compound of Example 32 is active at from 10 to 160 mg/kg and cures 6 mice out of 7 at 80 and 160 mg/kg.

the compound of Example 32, even when administered at a very high dose, is well tolerated and induces neither significant weight loss nor premature death. Thus, it exhibits:

very low general toxicity and an excellent therapeutic index.

2/Anti-tumour Activity of the Compounds in an Orthotopic Model of Human Lung Carcinoma NCI-H460 Implanted Intrapleurally The line NCI-H460, which originates from a human lung carcinoma of "not small cell" type, was supplied by the American Type Culture Collection (Frederick, USA). The cells are cultured in vitro in complete RPMI 1640 medium in Falcon flasks. On the day of the implantation, the cells are separated using trypsin, centrifuged and suspended in complete culture medium. The cells are then implanted in the pleural cavity of female Nude Balb/C mice ($10^6$ cells per mouse). The products are administered i.v. to groups of 6 animals on days 7 and 14 at the doses indicated. The anti-tumour activity is expressed in % T/C as defined above.

Table 3 lists the results obtained with the compound of Example 3 of the present Application (especially representative of the invention) and with the closest compound of the prior art as reference product.

TABLE 3

Anti-tumour activity of the compound of Example 3 and of the reference compound administered i.v. to human lung carcinoma NCI-H460 implanted intrapleurally.

| Test compounds | Doses mg/kg | T/C % |
|---|---|---|
| Example 3 | 0 | 100 |
| | 56.5 | 133 |
| | 80 | 147 |
| | 113 | 174 |
| | 160 | 181 |
| Reference product** | 0 | 100 |
| | 40 | 126 |
| | 56.5 | 145 |
| | 80 | 156 |
| | 113* | 186 |

*toxic dose (1 mouse dead during the treatments)
**the reference product is 1-[(2-dimethylaminoethyl)aminocarbonyl]-5,6-dimethyl-9-hydroxy-6H-pyrido-[4,3-b]carbazole dihydrochloride, that is to say the compound, in the form of the dihydrochloride, of Example 1 of patent application EP 0 591 058 A1.

A study of the Table shows that the reference product is active at from 40 to 80 mg/kg, the dose of 113 mg/kg being toxic. The compound of Example 3 is active and very well tolerated, even at a strong dose: administered twice at 160 mg/kg, it increases survival of the animals by 81%. The therapeutic index of the compound of Example 3 is thus excellent.

What is claimed is:

1. A compound selected from the group consisting of 1-[(2-dimethylaminoethyl)aminocarbonyl]-5,6-dimethyl-9-(4-carboxybutanoyloxy)-6H-pyrido[4,3-b]carbazole and 1-[(3-dimethylaminopropyl)aminocarbonyl]-5,6-dimethyl-9-(4-carboxybutanoyloxy)-6H-pyrido[4,3-b]carbazole and pharmaceutically-acceptable acid addition salts thereof.

2. A compound of claim 1 which is 1-[(3-dimethylaminopropyl)-aminocarbonyl]-5,6-dimethyl-9-(4-carboxybutanoyloxy)-6H-pyrido-[4,3-b]carbazole.

3. A compound of claim 1 which is 1-[(2-dimethylaminoethyl)-aminocarbonyl]-5,6-dimethyl-9-(4-carboxybutanoyloxy)-6H-pyrido-[4,3-b]carbazole dihydrochloride.

4. A pharmaceutical composition comprising as active ingredient a compound of claim 1 in association with a pharmaceutically-acceptable excipient or carrier.

5. A pharmaceutical composition comprising as active ingredient a compound of claim 2 in association with a pharmaceutically-acceptable excipient or carrier.

6. A pharmaceutical composition comprising as active ingredient a compound of claim 3 in association with a pharmaceutically-acceptable excipient or carrier.

7. Method-of-treating a living animal body afflicted with leukaemia, lung carcinoma or epidermoid carcinoma which comprises the step of administering to the living animal body an amount of a compound of claim 1 which is effective for alleviation of said affliction.

8. Method-of-treating a living animal body afflicted with leukaemia, lung carcinoma or epidermoid carcinoma which comprises the step of administering to the living animal body an amount of a compound of claim 2 which is effective for alleviation of said affliction.

9. Method-of-treating a living animal body afflicted with leukaemia, lung carcinoma or epidermoid carcinoma which comprises the step of administering to the living animal body an amount of a compound of claim 3 which is effective for alleviation of said affliction.

* * * * *

UNITED STATES PATENT AND TRADEMARK OFFICE
CERTIFICATE OF CORRECTION

PATENT NO. : 6,162,811
DATED : Dec. 19, 2000
INVENTOR(S) : C. Guillonneau, Y. Charton, E. Bisagni, G. Atassi, A. Pierre, N. Guilbaud It is certified that error appears in the above-identified patent and that said Letters Patent is hereby corrected as shown below:

Column 2, line 5: "form" should read: -- from --.
    Page 2, line 21

Column 2, line 63: "form" should read: -- from --.
    Page 3, line 25

Column 9, line 5: "formula H" should read:
    -- formula II --. Page 12, line 5

Column 13, line 9 (approx.): The line in the first
    formula that reads as follows:
    "$CONHCH_2CH_2N-N.....$" should read as:
    -- $CONHCH_2CH_2-N......$ --. Page 17, line 8

Column 20, lines 54, 59, and 64: The last word in
    the last sentence, "affiction.", should read:
    -- affliction. --. Page 2 of Examiner's
    Amendment, dated 15 May 2000, paragraph 2, b.,
    line 4.

Signed and Sealed this

Twenty-ninth Day of May, 2001

Attest:

NICHOLAS P. GODICI

Attesting Officer     Acting Director of the United States Patent and Trademark Office